(12) United States Patent
Scharf

(10) Patent No.: US 6,682,563 B2
(45) Date of Patent: Jan. 27, 2004

(54) SPINAL FIXATION DEVICE

(76) Inventor: Michael S. Scharf, 6636 Epping Forest Way North, Jacksonville, FL (US) 32217

( * ) Notice: Subject to any disclaimer, the term of this patent is extended or adjusted under 35 U.S.C. 154(b) by 12 days.

(21) Appl. No.: 10/090,990

(22) Filed: Mar. 4, 2002

(65) Prior Publication Data

US 2003/0167091 A1 Sep. 4, 2003

(51) Int. Cl.[7] ............................. A61F 2/44; A61B 17/56
(52) U.S. Cl. ..................................... 623/17.16; 606/61
(58) Field of Search .......................... 606/61, 69, 72, 606/73; 623/17.11, 17.12, 17.13, 17.14, 17.15, 17.16

(56) References Cited

U.S. PATENT DOCUMENTS

| | | | |
|---|---|---|---|
| 2,677,369 A | | 5/1954 | Knowles |
| 4,599,086 A | | 7/1986 | Doty |
| 4,743,256 A | | 5/1988 | Brantigan |
| 4,892,545 A | | 1/1990 | Day et al. |
| 4,917,704 A | | 4/1990 | Frey et al. |
| 4,955,908 A | | 9/1990 | Frey et al. |
| 5,324,290 A | * | 6/1994 | Zdeblick et al. ............ 606/61 |
| 5,344,421 A | * | 9/1994 | Crook .......................... 606/61 |
| 5,405,391 A | | 4/1995 | Hednerson et al. |
| 5,658,337 A | | 8/1997 | Kohrs et al. |
| 5,674,296 A | | 10/1997 | Bryan et al. |
| 6,066,175 A | | 5/2000 | Henderson et al. |
| 6,093,205 A | | 7/2000 | McLeod et al. |
| 6,156,067 A | | 12/2000 | Bryan et al. |
| 6,190,413 B1 | * | 2/2001 | Sutcliffe ................. 623/17.11 |
| 6,193,720 B1 | * | 2/2001 | Yuan et al. ................... 606/61 |
| 6,235,059 B1 | * | 5/2001 | Benezech et al. ........ 623/17.16 |
| 6,306,136 B1 | * | 10/2001 | Baccelli ........................ 606/61 |

* cited by examiner

Primary Examiner—David J. Isabella
(74) Attorney, Agent, or Firm—Thomas C. Saitta

(57) ABSTRACT

A spinal fixation device having a spacer member and a pair of fixation plate members, where the spacer member is a cage-like structure having a generally open and exposed interior defined by a pair of superior-inferior bores intersecting a lateral bore, the spacer member having a pair of opposing, generally planar, contact surface members having a plurality of anterior-posterior oriented, beveled ridges disposed thereon, with the fixation plate members attached to the anterior of the spacer member, the fixation plate members being asymmetrical and each containing a generally circular and a slotted screw-retaining aperture, with each disposed to one side of a lateral midline in reversed manner relative to each fixation plate member.

16 Claims, 3 Drawing Sheets

SPINAL FIXATION DEVICE

BACKGROUND OF THE INVENTION

This invention relates generally to the field of spinal fixation devices used to secure, stabilize or fuse adjacent vertebrae in a rigid relationship. Such devices include for example disc prostheses, cages, implants, rods and plates. More particularly, the invention relates to the smaller subset of such spinal fixation devices consisting of a combination of a plate structure, which is adapted to be affixed externally to the adjacent vertebrae, and an insert spacer structure, such as an implant prosthesis or cage, which is adapted to be positioned between the adjacent vertebrae.

The spinal column provides vertical support and protects the spinal cord. The column comprises a plural number of vertebrae separated by discs, which cushion and dampen compressive forces. In many circumstances, whether due to injury, disease, degenerative causes or congenital defect, it is necessary to surgically remove all or a portion of an intervertebral disc. A spacer device must then be inserted in place of the removed disc. Typically, the ends of the adjacent vertebrae are shaved, drilled or cut to produce a particular surface configuration, and the space between the adjacent vertebrae is then filled with a prosthetic structure, such as an artificial disc or an implant structure, often referred to as a cage. The cage has an open interior and relatively open or porous upper and lower ends or walls which contact the vertebrae, whereby the open interior is filled with bone grafting and bone fusion material such that the bone growth between the vertebrae is promoted to result in fusion of the adjacent vertebrae. In addition or alternatively, the adjacent vertebrae are fixed in a rigid relationship to each other, either through the promotion of bone growth between the vertebrae, by fixation means incorporated in the implant structure or by external fixation structures attached to the vertebrae, such as plates or rods.

In some circumstances it has been discovered that a spinal or vertebral fixation device which incorporates in combination an internal cage or implant structure rigidly joined to an external fixation plate structure is the optimum device for correcting the problem. Such a device provides the structure to separate and position the adjacent vertebrae the proper distance and in the proper spatial relationship after the disc has been removed, provides a cage structure whereby fusion of the adjacent vertebrae by natural bone growth results in fixing and maintaining the vertebrae in a rigid relationship, and provides an external structure attached to the adjacent vertebrae to secure the vertebrae during the bone growth process and to provide additional fixation means in support of the bone fusion. Examples of such devices are disclosed in U.S. Pat. No. 4,599,086 to Doty, U.S. Pat. No. 4,955,908 to Frey et al., U.S. Pat. No. 4,892,545 to Day et al., U.S. Pat. No. 5,674,296 to Bryan et al., U.S. Pat. No. 5,888,223 to Bray, Jr., and U.S. Pat. No. 6,066,175 to Henderson et al.

Doty shows a spine stabilization device which comprises a generally solid cylindrical intervertebral disc insert having flat upper and lower ends. An external plate member is attached to the side of the disc insert, the plate extending beyond both ends of the disc insert, whereby the plate can be affixed laterally to the adjacent vertebrae using screws. Frey et al. shows an intervertebral prosthesis comprising a kidney-shaped, generally solid, disc insert having pairs of symmetrical plates, designated as fishplates, which extend upward and downward from one edge of the disc insert, the plates being provided with screw apertures for lateral attachment to the exterior of the adjacent vertebrae. Day et al. shows a device similar to the Doty device, but wherein the external plate and the intervertebral disc insert are formed as an integral unit. Bryan et al. shows a spinal disc prosthesis where the disc prosthesis is maintained in place by the combination of an annular member and two independent L-shaped supports, each support being attached to a vertebra. The disc prosthesis and the annular member are not secured to the vertebrae. Bray, Jr., shows an anterior stabilization device having a disc-shaped intervertebral spacer cage having a pair of superior lips and a single inferior lip, the lips provided with screw apertures for external fixation to the adjacent vertebrae. The inferior lip is centrally disposed relative to the superior lips, the superior lips being circumferentially spaced. Henderson et al. shows an intervertebral chamber or cage in combination with an external mounting plate. The mounting plate is provided with symmetrically disposed, equally sized screw apertures to receive mounting screws for affixing the plate to the adjacent vertebrae.

While the above referenced devices provide for an integral spinal fixation device having an intervertebral disc or cage and an external mounting plate, the particular structures and configurations shown present problems when affixing the devices to the spine of a patient. In particular, the known devices do not provide mechanisms to account for variations in the size, shape, separation distance and other vertebral factors, such that a surgeon is often forced to affix the devices in a less than optimum manner. For example, where multiple devices must be utilized to secure three or more adjacent vertebrae, the size and configuration of the plates may be too large, such that adjacent devices cannot be placed close enough together. It is an object of this invention therefore, to provide a spinal or vertebral fixation device which comprises the combination of an integral spacer cage member and external mounting plates, where the configuration of the insert cage and the mounting plates optimizes the fixation characteristics in order to provide for secure attachment and relative fixation of the adjacent vertebrae. It is a further object to provide such a device where the configuration of the plate members is such that multiple devices can be utilized on a single spinal column with the intervertebral cages disposed in relatively close proximity without having the plate members interfere and without reducing the efficacy of the mounting mechanism. It is a further object to provide such a device where the screw apertures in the mounting plates are of differing sizes and configurations, such that the surgeon has options to position the mounting screws in the most effective locations and alignments on the vertebrae, and where the screw apertures are beveled in a manner which causes compression of the vertebrae to the cage to enhance stability.

SUMMARY OF THE INVENTION

The invention is in general a spinal fixation device or intervertebral implant member which is adapted to be inserted between adjacent vertebrae in place of a natural intervertebral disc, such that the adjacent vertebrae are secured in a fixed manner to each other. The spinal implant member comprises in general a spacer member and fixation plate members, the spacer member comprising an apertured cage structure adapted to be inserted between the adjacent vertebrae and the fixation plate members having asymmetrical perimeters and comprising screw-receiving apertures adapted to be secured to each of the adjacent vertebrae.

The apertured cage structure of the spacer member comprises a main body, opposing vertebral contact surfaces on the superior and inferior ends of the main body, which are preferably generally planar and parallel to each other, a plurality of linear, parallel, beveled ridge members extending outwardly from each of the contact surfaces and oriented in the anterior-posterior direction, and an open interior, formed preferably for example by a pair of large openings or bores extending through the contact surfaces in the superior-inferior direction interconnected with a large lateral opening or bore extending through the main body. The contact surfaces are preferably rounded on the posterior portion of the lateral walls.

The fixation plate members are connected to the anterior side of the main body and extend in the superior-inferior direction. Each fixation plate member comprises a circular screw-receiving aperture and an elongated or slotted screw-receiving aperture. To accommodate the extended length of the slotted screw-receiving aperture, one side of each fixation plate member is of greater length than the other side, such that each fixation plate member is laterally asymmetrical. The slotted screw-receiving apertures are disposed on opposite sides of the device, which enables adjacent devices to be more closely arranged along the spinal column.

DETAILED DESCRIPTION OF THE INVENTION

Figure 1:
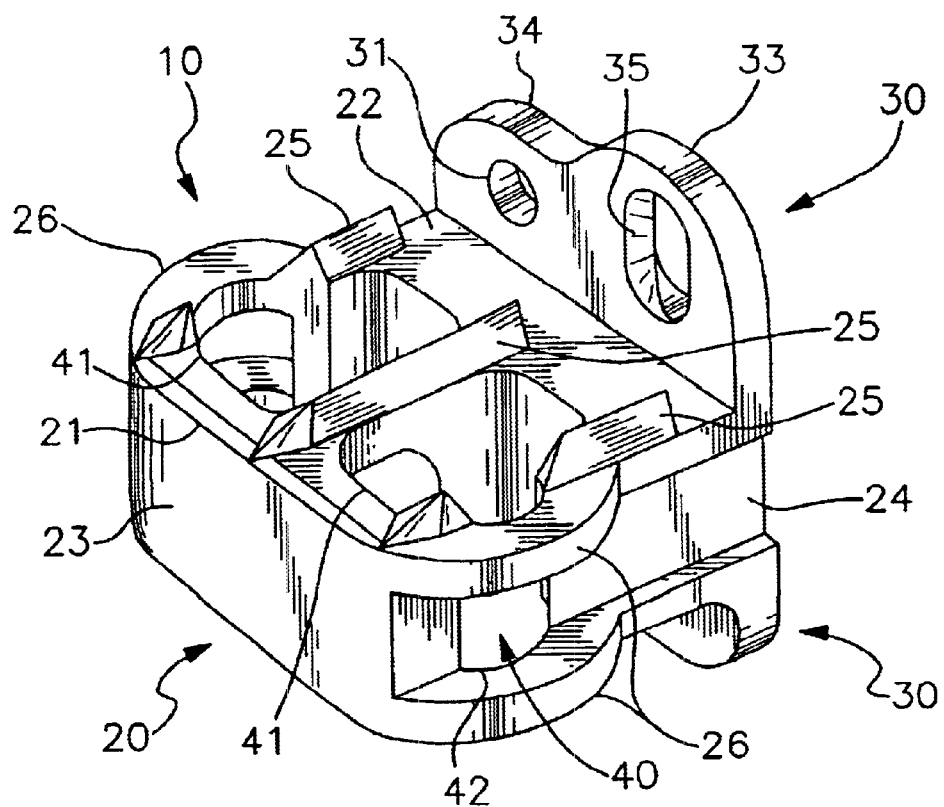
FIG. 1 is a perspective view of the spinal fixation device.

With reference to the drawings, the invention will now be described in detail with regard for the best mode and the preferred embodiment. As used herein, the term anterior shall mean situated in front of or toward the front of the spinal column, the term posterior shall mean situated behind or toward the rear of the spinal column, the term superior shall mean situated above or toward the top of the spinal column, the term inferior shall mean situated below or toward the bottom of the spinal column, and the term lateral shall mean situated to the left and right sides of the spinal column. Thus the terms are to be given their standard and accepted meanings within the medical community. When these terms are used in reference to describing elements or components of the invention, the terms provide directional definition as for the invention when properly implanted and affixed to the spinal column.

The invention is a spinal fixation device 10 which is adapted to be inserted between adjacent vertebrae 91 to replace a natural intervertebral disc which has been damaged or removed for medical purposes, whereby the spinal fixation device 10 maintains the proper separation distance between the vertebrae 91, provides a vertical load bearing structure, and is secured to the adjacent vertebrae 91 in a rigid, stabilizing manner such that the adjacent vertebrae 91 are in a rigid, fixed relationship with each other. The spinal fixation device 10 is composed of a bio-acceptable metal, ceramic or polymer composite material of suitable strength and durability.

The spinal fixation device 10 comprises in combination a spacer member 20, also referred to as a cage or disc implant member, and fixation plate members 30. While described herein as a pair of fixation plate members 30 which extend in opposing directions, it is to be understood that the two fixation plate members 30 may also be defined as a single or integral plate member 30 joined to the spacer member 20, in that the resulting structure would serve the same purpose. The spacer member 20 is the portion of the device 10 which is positioned between the vertebrae 91 to replace the disc in order to properly separate, support and stabilize the vertebrae 91, while the fixation plate members 30 are disposed anteriorly to the spacer member 20 when the spacer member 20 is placed between the vertebrae 91 such that the fixation plate members 30 abut and are secured on the anterior of the adjacent vertebrae 91 in standard manner using bone screws 51 or like fastening members in order to immobilize the adjacent vertebrae 91 relative to each other.

Figure 2:
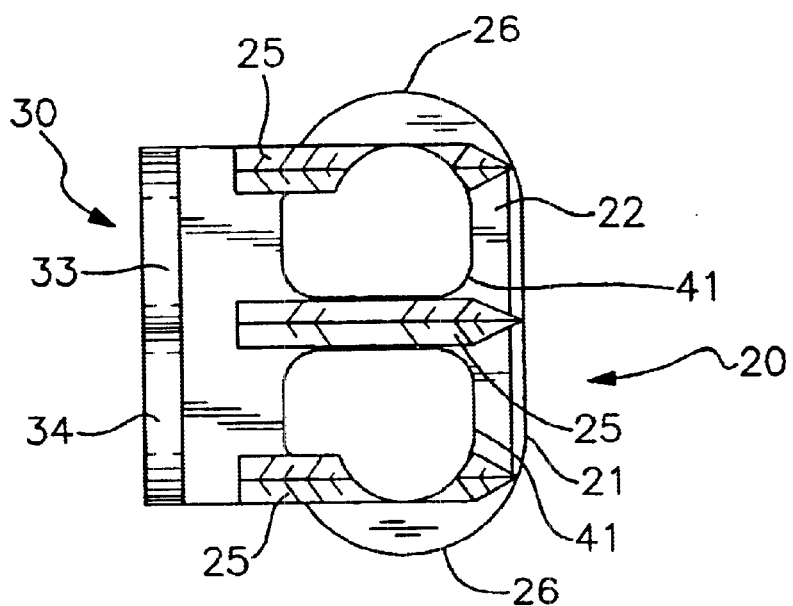
FIG. 2 is a superior view of the device.

The spacer member 20 comprises an apertured, generally hollow, main body member 21 having an exposed, open interior 40, which may be described as having a cage-like structure, the purpose of which is to allow for bone graft material, bone morphogenic protein or the like to be placed therein while maintaining sufficient rigidity and load bearing characteristics. The spacer member 20 further comprises two contact surface members 22, one superior and one inferior, which may also be referred to as end plate members, a posterior wall 23 and opposing lateral walls 24. The contact surface members 22 are adapted to abut the opposing end surfaces of the adjacent vertebrae 91, which have been provided with notches or cut-outs having correspondingly configured surfaces by known routing methods. The contact surface members 22 are preferably generally planar and disposed parallel to each other, although it is also possible for the contact surface members 22 to be non-parallel such that the spacer member 20 is wedge-shaped. The main body member 21 is provided with a pair of bores 41 oriented in the superior-inferior direction such that they extend through the superior and inferior contract surface members 22. The main body member 21 is also provided with a lateral bore 42 oriented in the lateral direction such that it extends through both lateral walls 24. The superior-inferior bores 41 and the lateral bore 42 interconnect to define a relatively large open interior 40 within main body member 21 which is externally exposed. The superior-inferior bores 41 are preferably equally sized and symmetrically disposed such that the main body member 21 has a generalized figure-8 configuration when viewed from the superior or inferior direction, as shown in FIG. 2. This configuration is further enhanced by providing rounded shoulder members 26 on the posterior portions of the lateral walls 24, where the superior surface of the superior shoulder members 26 and the inferior surface of the inferior shoulder members 26 comprise a portion of the contact surface members 22. In this manner the contact surface members 22 are of greater width laterally on the posterior side of the main body member 21 in order to better conform to the general configuration of a vertebra.

Figure 3:
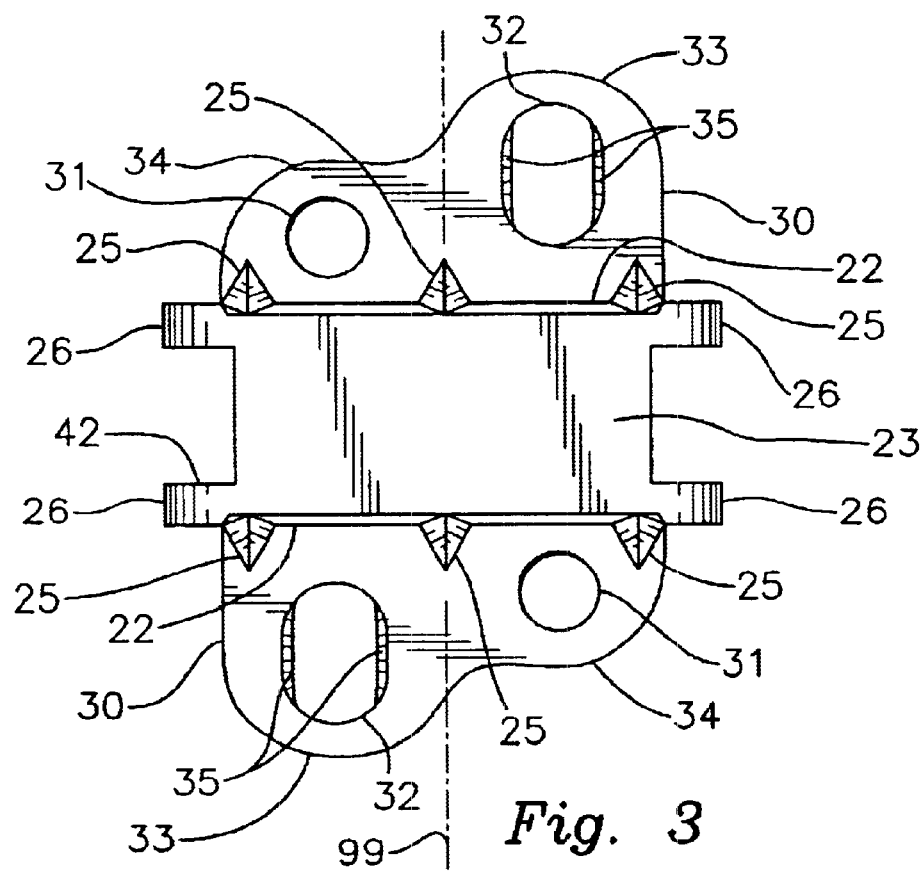
FIG. 3 is a posterior view of the device.
Figure 4:
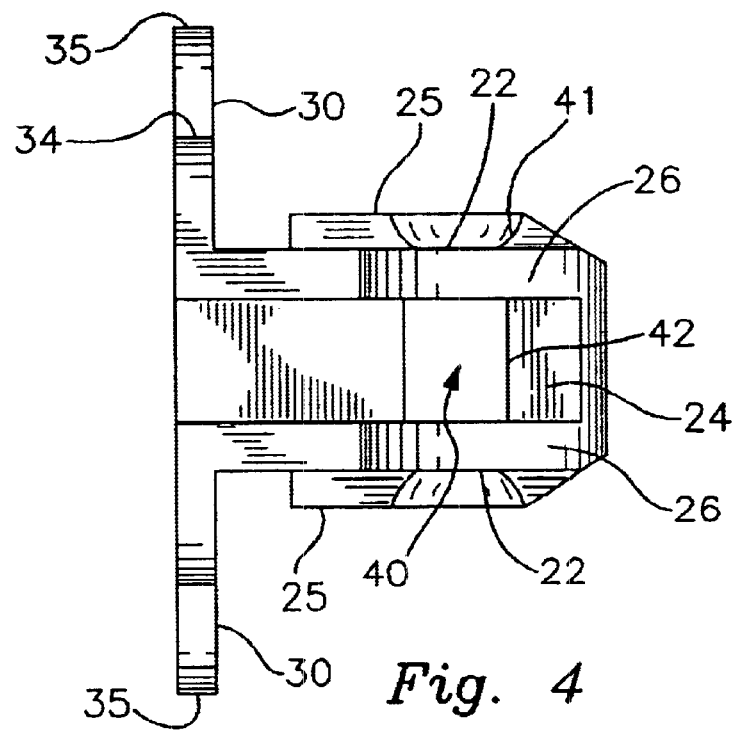
FIG. 4 is a lateral view of the device.

Most preferably the spacer member 20 further comprises a plurality of linear, beveled ridge members 25 disposed externally on both contact surface members 21. The ridge members 25 have a generally triangular cross-sectional configuration, as seen in FIG. 3, and present a knife-like edge in the superior and inferior directions. The ridge members 25 are parallel to each other and extend in the anterior-posterior direction. Preferably, three ridge members 25 are provided on each contact surface member 21, with one disposed centrally between the two superior-inferior bores 41 and the other two disposed along the lateral edges of the superior-inferior bores 41, for a total of six ridge members 25. The ridge members 25 cut into the prepared surfaces of the vertebrae 91 and preclude lateral or rotational movement of the device 10 relative to the vertebrae 91 once the spinal fixation device 10 is implanted.

Adjoined to the anterior side of the main body member 21 of the spacer member 20 are a pair of fixation plate members 30, with one extending in the superior direction and the other extending in the inferior direction from the contact surface members 21. The fixation plate members 30 are preferably generally planar and are relatively thin in the anterior-posterior direction. Each fixation plate member 30 comprises a generally circular screw-receiving aperture 31 and a generally elongated or slotted screw-receiving aperture 32 of greater length than the diameter of the circular screw-receiving aperture 31, where the circular screw-receiving aperture 31 is positioned to one side of the lateral midline 99 of the fixation plate member 30 and the slotted screw-receiving aperture 32 is positioned on the other side of the lateral midline 99, as shown in FIG. 3. Preferably, the slotted screw-receiving apertures 32 are provided with beveled shoulders 35 which causes the adjoining vertebrae 91 to be compressed for enhanced stability when the bone screws 51 are tightened. Preferably the slotted screw-receiving apertures 32 are wider laterally than the circular screw-receiving apertures 31 in order to receive larger bone screws 51. The slotted screw-receiving apertures 32 are of greater length in the superior-inferior direction than the circular screw-receiving apertures 31, and thus the fixation plate members 30 are asymmetrical about the lateral midline 99 such that a long or extended plate portion 33 contains the slotted screw-receiving aperture 32 and a short or recessed plate portion 34 contains the circular screw-receiving aperture 31. The slotted screw-receiving aperture 32 of the superior fixation plate member 30 is positioned on the opposite side of that of the slotted screw-receiving aperture 32 of the inferior fixation plate member 30, and likewise the circular screw-receiving aperture 31 of the superior fixation plate member 30 is positioned on the opposite side of that of the circular screw-receiving aperture 31 of the inferior fixation plate member 30, such that they are reversed relative to the pair of fixation plate members 30.

Figure 5:
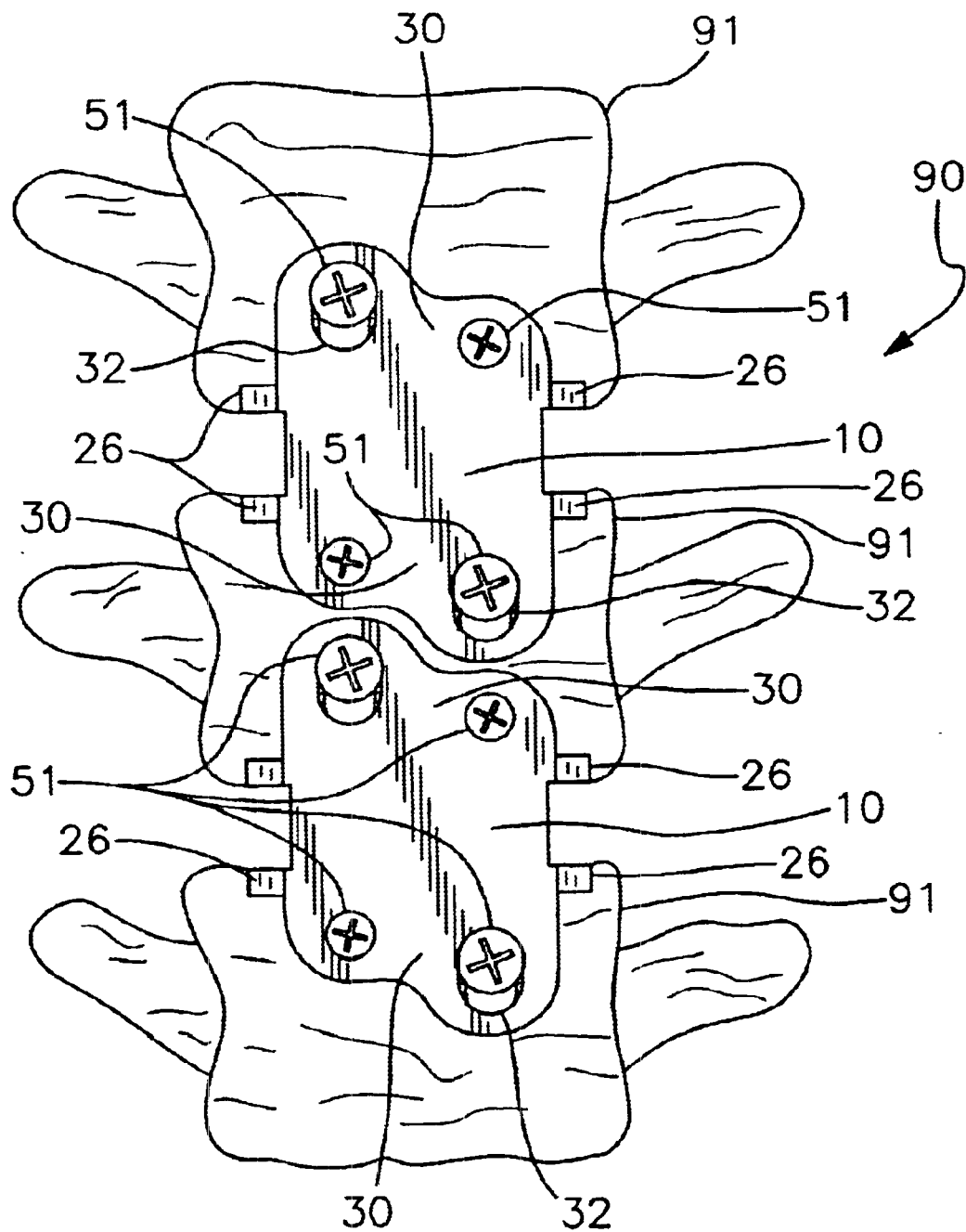
FIG. 5 is an anterior view showing a pair of devices as affixed to a spinal column.

The asymmetrical configuration of the fixation plate members 30 is important in circumstances where two spinal fixation devices 10 must be affixed to join three contiguous vertebrae 91, as shown in FIG. 5. In circumstances where the superior-inferior separation distance between adjacent vertebrae 91 is relatively small, such as with short people or children, the asymmetrical shape allows the adjacent spinal fixation devices 10 to be more closely abutted. The extended plate portion 33 of the inferior fixation plate member 30 of the superior spinal fixation device 10 abuts the recessed plate portion 34 of the adjacent superior fixation plate member 30 of the inferior spinal fixation device 10, and the recessed plate portion 34 of the inferior fixation plate member 30 of the superior spinal fixation device 10 abuts the extended plate portion 33 of the adjacent superior fixation plate member 30 of the inferior spinal fixation device 10, thereby allowing the larger bone screws 51 of both spinal fixation devices 10 to be inserted more toward the interior of the middle vertebra 91, which decreases the likelihood of failure of the securing means.

It is contemplated that equivalents and substitutions for certain elements set forth in exemplary fashion above may be obvious to those skilled in the art without departing from the essence of the invention, and therefore the true scope and definition of the invention is to be as set forth in the following claims.

I claim:

1. A spinal fixation device comprising:
    a spacer member comprising a main body member having an exposed open interior and a pair of contact surface members;
    a pair of fixation plate members joined to said spacer member, each of said fixation plate members comprising an extended plate portion and a recessed plate portion, wherein said extended plate portion of one of said fixation plate members is on the side opposite that of said extended plate portion of the other of said fixation plate members;
    a slotted screw-receiving aperture disposed in each of said extended plate portions; and
    a circular screw-receiving aperture disposed in each of said recessed plate portions.

2. The device of claim 1, further comprising at least one beveled ridge member disposed on each of said contact surface members.

3. The device of claim 2, wherein said exposed open interior is defined by intersecting bores.

4. A spinal fixation device comprising:
    a spacer member comprising a main body member having an exposed open interior, a superior contact surface member and an inferior contact surface;
    a pair of fixation plate members joined anteriorly to said spacer member, one of said fixation plates extending superiorly and the other of said fixation plates extending inferiorly, each of said fixation plate members comprising a lateral midline, an extended plate portion and a recessed plate portion, wherein said lateral midline is between said extended plate portion and said recessed portion, wherein said extended plate portion of said superiorly-extending fixation plate member is on the lateral side opposite that of said extended plate portion of said anteriorly-extending fixation plate member
    a slotted screw-receiving aperture disposed in each of said extended plate portions; and
    a circular screw-receiving aperture disposed in each of said recessed plate portions.

5. The device of claim 4, further comprising at least one beveled ridge member disposed on said superior and inferior contact surface members, wherein said at least one beveled ridge members are parallel.

6. The device of claim 4, wherein said exposed open interior is defined by the intersection of a pair of superior-inferior bores extending through said superior and inferior contact surface members and a lateral bore extending through said main body.

7. The device of claim 6, wherein said at least one beveled ridge member disposed on said superior and inferior contact surface members comprises three beveled ridge members disposed on said superior contact surface and three beveled ridge members disposed on said inferior contact surface.

8. The device of claim 4, wherein said slotted screw-receiving apertures further comprise beveled shoulders.

9. The device of claim 4, wherein said superior and inferior contact surface members further comprise laterally-extending rounded shoulder members.

10. A spinal fixation device comprising:
    a spacer member adapted to be inserted between adjacent vertebrae in a spinal column as replacement for a removed intervertebral disc, said spacer member comprising a main body member having an exposed open interior, a generally planar superior contact surface member adapted to abut a superior vertebra and a generally planar inferior contact surface adapted to abut an inferior vertebra;

a pair of fixation plate members joined anteriorly to said spacer member, one of said fixation plates extending superiorly from said spacer member and adapted to abut and be secured to a superior vertebra and the other of said fixation plates extending inferiorly and adapted to abut and be secured to an inferior vertebra, each of said fixation plate members comprising a lateral midline, an extended plate portion and a recessed plate portion, wherein said lateral midline is between said extended plate portion and said recessed portion, wherein said extended plate portion of said superiorly-extending fixation plate member is on the lateral side opposite that of said extended plate portion of said anteriorly-extending fixation plate member; and a slotted screw-receiving aperture disposed in each of said extended plate portions and adapted to receive a screw to secure said fixation plate member to either a superior or inferior vertebra;

and a screw disposed within each said slotted screw receiving aperture, said screw adapted to be driven into either a superior or inferior vertebra.

11. The device of claim 10, further comprising a circular screw-receiving aperture disposed in each of said recessed plate portions and adapted to receive a screw to secure said fixation plate member to either a superior or inferior vertebra;

and a screw disposed within each said circular screw receiving aperture, said screw adapted to be driven into either a superior or inferior vertebra.

12. The device of claim 10, further comprising at least one beveled ridge member disposed on said superior and inferior contact surface members, wherein said at least one beveled ridge members are parallel.

13. The device of claim 10, wherein said exposed open interior is defined by the intersection of a pair of superior-inferior bores extending through said superior and inferior contact surface members and a lateral bore extending through said main body.

14. The device of claim 13, wherein said at least one beveled ridge member disposed on said superior and inferior contact surface members comprises three beveled ridge members disposed on said superior contact surface and three beveled ridge members disposed on said inferior contact surface.

15. The device of claim 10, wherein said slotted screw-receiving apertures further comprise beveled shoulders.

16. The device of claim 10, wherein said superior and inferior contact surface members further comprise laterally-extending rounded shoulder members.

* * * * *